US005783583A

United States Patent [19]

Simon

[11] Patent Number: 5,783,583
[45] Date of Patent: Jul. 21, 1998

[54] 17-(CYCLOPROPYLMETHYL)-4,5ALPHA-EPOXY-6-METHYLENEMORPHINAN-3,14-DIOL, HYDROCHLORIDE SALT FOR THE PURPOSE OF RAPID NARCOTIC DETOXIFICATION

[76] Inventor: David Lew Simon, P.O. Box 618, Mansfield Center, Conn. 06250

[21] Appl. No.: 631,081

[22] Filed: Apr. 12, 1996

[51] Int. Cl.$^6$ .......................... A01N 43/42; A61K 31/44
[52] U.S. Cl. ........................ 514/282; 514/281; 546/45
[58] Field of Search ........................... 514/282, 281; 546/45

[56] References Cited

U.S. PATENT DOCUMENTS

| | | | |
|---|---|---|---|
| 3,896,226 | 7/1975 | Fishman | 424/260 |
| 4,535,157 | 8/1985 | Meltzer et al. | 546/44 |
| 4,987,136 | 1/1991 | Kreek et al. | 514/282 |
| 5,272,149 | 12/1993 | Stalling | 514/255 |

OTHER PUBLICATIONS

DuPont Pharma, package insert fo Narcan (naloxone), Feb. 1995.
Partidge et al., "Pulmonary Edema Following Low–dose Naloxone Administration", Anesthesiology, vol. 65, No. 6, pp. 709–710, 1986.
DuPont Pharma, package insert for Revia (naltrexone), pp. 1–2, Jan. 1995.
Taff, "Pulmonary Edema Following Naloxone Administration in a Patient Without Heart Disease", Anesthesiology, 59, 576–77, 1983.
San et al., "High Risk of Ultrashort Noninvasive Opiate Detoxification", Am. J. Psychiatry 152, p. 956, Jun. 1995.
Brewer, C., "Ultra–rapid, antagonist–precipitated opiate detoxification under general anaesthesia or sedation", Addiction Biology 2/3, pp. 291–302, 1997.
Gerra et al., "Clonidine and Opiate Receptor Antagonists in the Treatment of Heroin Addiction", Journal of Substance Abuse Treatment, vol. 12, No. 1, pp. 35–41, 1995.
Loimer et al., "Continuous Naloxone Administration Suppresses Opiate Withdrawal Symptoms In Human Opiate Addicts During Detoxification Treatment", 1989 pp. 81–86.
Text—*Opioid Peptides in Substance Abuse* by Jozsef I. Szekely, CRC Press, Inc., p. 160 (1994).
Article—Spanagel et al.—"Opposing tonically active endogenous opioid systems modulate the mesolimbic dopaminergic pathway" *Proc. Natl. Acad. Sci. USA* vol. 89, p. 2046, Mar. 1992.

Article—Pan et al. "Cellular mechanism for anti–analgesic action of agonists of the k–opioid receptor" *Nature* vol. 389/25 Sep., pp. 382–385 (1997).
Article—Kreeks et al. "Orally Administered opioid antagonists reverse both mu and kappa opioid agonist delay of gastrointestinal transit in the guinea pig" *Life Sciences*, vol. 56, No. 14, pp. 1187–1192, 1995.
Article—Arts et al. "Inhibition of the Antianalgesic Action of Dynorphin A in Mice by Cholera Toxin" *Pharmacology Biochemistry and Behavior*, vol. 46, pp. 623–629, 1993.
Article—Bakashi et al. "Dynorphin A–(1–17) Induces Alterations in Free Fatty Acids, Excitatory Amino Acids, and Motor Function Through An Opiate–Receptor–Mediated Mechanism" *The Journal of Neuroscience*, Dec. 1990, 10(12): 3793–3800.
Article—Behrmann et al. "A Comparison of YM–14673, U–50488H, and Nalmefene after Spinal Cord Injury in the Rat" *Experimental Neurology* 119, 258–267 (1993).
Article—Ohnishi et al. "Aquaretic Effect of the Stable Dynorphin–A analog E2078 in the Human" *The Journal of Pharmacology and Experimental Therapeutics* vol. 270, No. 1, Mar. 19, 1994.
Article—Salas et al. "[N–Methyl–Tyr$^1$, N–Methyl–Arg$^7$–D–Leu$^8$]–Dynorphin–A–(1–8)Ethylamide, a Stable Dynorphin Analog, Produces Diuresis by Kappa–Opiate Receptor Activation in the Rat" *The Journal of Pharmacology and Experimental Therapeutics* vol. 262, No. 3, 1992.
Article—Wang et al. "Contribution of Alpha–2 Adrenoceptors to Kappa Opioid Agonist–Induced Water Diuresis in the Rat" *The Journal of Pharmacology and Experimental therapeutics* vol. 270, 1994.
Article—O'Connor et al. Rapid and Ultrarapid Opioid Detoxification Techniques *JAMA*, Jan. 21, 1998—vol. 279, No. 3.

*Primary Examiner*—Kimberly Jordan
*Assistant Examiner*—Dwayne C. Jones
*Attorney, Agent, or Firm*—McCormick, Paulding & Huber

[57] ABSTRACT

Methods whereby the narcotic antagonist 17-(cyclopropylmethyl)-4,5alpha-6-methylenemorphinan-3, 14-diol,hydrochloride salt and other narcotic antagonists are used for chemically precipitating a withdrawal response in human beings addicted to exogenous narcotics and who are currently using exogenous narcotics.

6 Claims, No Drawings

17-(CYCLOPROPYLMETHYL)-4,5ALPHA-EPOXY-6-METHYLENEMORPHINAN-3,14-DIOL, HYDROCHLORIDE SALT FOR THE PURPOSE OF RAPID NARCOTIC DETOXIFICATION

FIELD OF INVENTION

The present invention relates to novel methods using a chemical compound which possesses special characteristics that makes it uniquely ideal for active and rapid medical detoxification of human beings addicted to exogenous narcotic drugs. The general classification of said chemical compound is known as narcotic antagonists.

BACKGROUND OF THE INVENTION

Prior Art

An opiate is a remedy containing or derived from opium, *Dorland's Illustrated Medical Dictionary*, 26th edition. An opioid is any synthetic narcotic that has opiate-like activities but is not derived from opium, *Dorland's Illustrated Medical Dictionary*, 26th edition. Either of said drugs may be classified as a narcotic. Many human beings are addicted to exogenous narcotics and want to become free of this addiction, but traditional withdrawal techniques result in high rates of dropout and early relapse. In order to improve the success of becoming free from addiction to exogenous narcotics, newer techniques have been promulgated which offer to lower the dropout rate from treatment and the relapse rate relating to failed treatment and further use of exogenous narcotics. In general, the process by which an addicted human being is ridded of the effects of an exogenous narcotic and undergoes the resultant process of withdrawal, is termed detoxification. Techniques for detoxification have been used whereby a narcotic antagonist is administered to a human being who is addicted to narcotics and currently using exogenous narcotics such that said narcotic antagonist displaces the exogenous narcotic from physiologic receptors in the body of the addicted human being, thus freeing up said exogenous narcotic from said receptors and allowing said exogenous narcotic to be excreted from the body by normal bodily mechanisms, as seen with LOIMER, LENZ et al., *American Journal of Psychiatry*, (1991), 148(7), 933–35. One of these techniques for detoxification involves the administration of the chemical compound (−)-17-Allyl-4,5alpha-epoxy-3,14-dihydroxy=morphinan-6-one hydrochloride, known as naloxone, in conjunction with anesthesia, shown by LOIMER, HOFMANN, et al, *American Journal of Psychiatry*, (1993), 150(5), 839. Naloxone is used for this purpose because its salt preparation can be administered intravenously, but it is a bad drug for this purpose for two reasons: Firstly, it has a short chemical half-life in the human body so that its effects are too short-lasting, as shown in NARCAN package insert, ©1995, Dupont Pharma; Secondly, it is associated with life-threatening adverse reactions, as shown by TAFT, *Anesthesiology*, (1983), 59, 576–77, and PARTRIDGE, et al., *Anesthesiology*, (1986), 65, 709–10, notably when used for the purpose of detoxification as indicated by SAN et al., *American Journal of Psychiatry*, (1995), 152, 956. A chemical compound related to naloxone in which the methyl group on the nitrogen atom is replaced by a cyclopropylmethyl group, known as naltrexone, has been used for this purpose by LEGARDA et al., *Drug Alcohol Depend* (1994), 35(2), 91–93, but it too has a major drawback: Naltrexone is known to cause hepatocellular injury, stated in REVIA.™ package insert, ©1995, DuPont Pharma. Many human beings addicted to narcotics are at risk for abnormalities of liver function. Therefore, naltrexone is potentially very harmful to this group of human beings.

The chemical compound 17(cyclopropylmethyl)-4,5alpha-epoxy-6-methylenemorphinan-3,14diol, hydrochloride salt, known as nalmefene, may be used for detoxifying human beings addicted to narcotics in association with anesthesia because it is able to be administered intravenously, and because it does not cause hepatocellular injury as does naltrexone, shown by REVIA™ package insert, and REVEX™ package insert, April, 1995, Ohmeda Pharmaceutical Products Division, Inc. Also, because it is longer acting than naloxone, nalmefene is very favorable to naloxone for the purpose of rapid detoxification of narcotic addicts. Of all available narcotic antagonists, nalmefene is uniquely suited for the purpose of rapid narcotic detoxification. Despite this, nalmefene has not been used in published reports for the purpose of rapid narcotic detoxification, but naltrexone and naloxone have been used for this purpose in published reports. Nalmefene is not marketed by its manufacturer for narcotic detoxification, as evidenced by REVEX™ package insert. Nalmefene's use as a drug for rapid detoxification is not obvious to its manufacturer or investigators in the field of narcotic detoxification. Nalmefene is not a new chemical compound.

The new, innovative use of a previous invention, that is, using nalmefene for rapid narcotic detoxification, is distinctly different from the proposed use of nalmefene as described by the distributing pharmaceutical company Ohmeda Pharmaceutical Products Division, Inc. In relation to use of nalmefene in patients physically dependent to narcotics, Ohmeda warns that nalmefene "is known to have the potential to produce acute withdrawal symptoms and therefore should be used with extreme caution in patients with known physical dependence on opioids." Furthermore and more definitively, the company specifically states that nalmefene "is contraindicated in patients with a known hypersensitivity to the product," as stated in REVEX™ package insert and REVEX™ (nalmefene HCL injection) Product Monograph, ©1995, Ohmeda Pharmaceutical Division, Inc. By definition, a narcotic addict who is physically dependent upon exogenous opioids and who is currently using said exogenous opioids, is hypersensitive to nalmefene or other narcotic antagonists. Therefore, the company in charge of marketing nalmefene specifically warns against using it for the purpose of rapid detoxification, providing further evidence of the unobviousness of the present invention.

Nalmefene has been marketed for use in reversing respiratory depression and other effects of narcotic overdose. It is also marketed for reversing the respiratory depression sometimes seen with the administration of intrathecal narcotics. Nalmefene is not marketed for the purpose of detoxification. Naltrexone is marketed for use in treatment of alcoholism and for the long term treatment of human beings previously addicted to narcotics who have already undergone withdrawal and detoxification. Dupont Pharma, the pharmaceutical company which distributes naltrexone in the United states lists the following warning regarding naltrexone in capitalized letters: "DO NOT ATTEMPT TREATMENT WITH REVIA UNLESS, IN THE MEDICAL JUDGMENT OF THE PRESCRIBING PHYSICIAN, THERE IS NO REASONABLE POSSIBILITY OF OPIOID USE WITHIN THE PAST 7–10 DAYS," seen in REVIA package insert. Therefore, a reasonable physician would assume that naltrexone is not to be used for the purpose of inducing withdrawal as for detoxification. Nalmefene, which has come to market since the introduction of naltrexone, carries no information contrary to said warning for naltrexone. Because nalmefene and naltrexone are both chemically related narcotic antagonists with similar pharmacologic properties, a typical reasonable physician would assume that the same warning holds true for nalmefene as for naltrexone. Therefore, the present invention is not obvious to a typical reasonable physician.

Parenteral administration of a narcotic antagonist has been shown to produce a withdrawal syndrome which is different from the withdrawal syndrome following mere cessation of exogenous narcotic intake by virtue of the subsiding of symptoms in about two hours with said antagonist, as stated by GOODMAN et al., Goodman and Gilman's *The Pharmacological Basis of Disease*, (1980), 6th edition, 523–24. This is a significantly less amount of time for said symptoms to subside than without parenteral narcotic antagonist. This is very important because withdrawal from mere abstinence of exogenous narcotics without said narcotic antagonist can cause a prolonged and unpleasant withdrawal reaction for addicts which may last many days. The process can be shortened to 2–4 hours by administration of narcotic antagonists as shown by LEGARDA et al., and described by GOODMAN et. al. However, if said narcotic antagonists were medically administered to awake narcotic addicts, the symptoms would be unbearable or even life threatening. This is because human beings addicted to narcotics and currently using narcotics are hypersensitive to narcotic antagonists. This hypersensitivity is evidenced by the sympathetic nervous system becoming extremely excited when an addicted human being currently using narcotics is administered a narcotic antagonist. However, the unpleasant symptoms can be effectively masked by medically administering sedatives or anesthetics, and dangerous side effects can be attenuated by anesthesia. Therefore, a promising treatment for narcotic addiction is to place an addict in a state of unconsciousness and then to medically administer a narcotic antagonist. This results in a rapid, complete withdrawal process with minimal or no symptoms as shown by LEGARDA, et al., and PRESSLICH, et al., *Clinical Toxicology*, (1989), 27, 263–70, and LOIMER, SCHMIDT et al., *British Journal of Psychiatry*, (1988), 153, 851–52. However, when naloxone is used, it is necessary to use a constant infusion of naloxone because it is so short acting as evidenced by PRESSLICH et al., and LOIMER, SCHMIDT, et al. When a longer acting narcotic antagonist is infused over a short time, 2 hours for example, the effects of the longer acting narcotic antagonist are still present many hours after the infusion is discontinued. This is important because it is essential for detoxification that the effects of said narcotic antagonist are still in force after the human being regains consciousness after such a short amount of time undergoing withdrawal as embodied in the present invention. When an infusion of a shorter acting narcotic antagonist such as naloxone is discontinued, the effects of said shorter acting narcotic antagonist dissipate shortly thereafter. A shorter acting narcotic antagonist infusion, such as an infusion with naloxone, must therefore be infused for a much longer time. This would require greater utilization of resources for equipment and care by health workers, which increases the costs of delivering the treatment. Cost control is a major issue in health care delivery. Also, as seen by SAN et al., naloxone has been associated with very serious adverse effects when used in this way. Naltrexone is associated with hepatocellular injury. Of these three narcotic antagonists, namely naloxone, naltrexone and nalmefene, naltrexone is most noted for causing hepatocellular injury, which can be seen by reviewing the packages inserts of NARCAN, REVIA™ and REVEX™.

After the process of detoxification has been completed in a human being as described, said human being is typically prescribed a regimen of taking a narcotic antagonist orally in pill, tablet or capsule form for some time which improves abstinence from exogenous narcotics and decreases relapse rates to more use of exogenous opioids as shown by GERRA, et al. *Journal of Substance Abuse and Treatment* (1995), 12(1), 35–41.

STALLING, U.S. Pat. No. 5,272,149, relates to novel methods for the purpose of rapid detoxification, withdrawal and symptom management of addicted patients. However, STALLING's method is needlessly complicated and complex. He states that first an autonomic nervous system blocking agent be administered, followed by a short-acting narcotic antagonist, followed by a combination narcotic agonist-antagonist, in a repeating fashion and so forth over many hours. His method is tedious, cumbersome and unnecessary. Furthermore, it takes many times longer to accomplish detoxification than with the present invention. In addition, STALLING's method includes multiple urinalysis examinations over the course of the procedure. These urinalysis examinations clearly are not needed and they represent a waste of resources. The present invention presents a way of achieving rapid narcotic detoxification in significantly less steps, which can be accomplished is less time and at less expense. STALLING's invention, while being unnecessarily complicated and complex, is also too vague: He describes administering an autonomic nervous system blocking agent, but he does not describe whether the sympathetic portion of the autonomic nervous system should be blocked or the parasympathetic portion of said autonomic nervous system. This is an important distinction. The present invention does not necessarily require a specific autonomic nervous system blocking agent because anesthesia or significant sedation is known to attenuate the excited response of the sympathetic nervous system. Anesthesia or significant sedation given during rapid detoxification greatly alleviates what would otherwise be an excruciating process, that is, medically administering a narcotic antagonist to a patient addicted to narcotics who is currently using exogenous narcotics. Anesthesia or significant sedation must be given for detoxification over such a short period of time as part of a humane and compassionate treatment because the withdrawal response precipitated by the narcotic antagonist is so severe. Importantly, STALLING's method does not include the use of 17(cyclopropylmethyl)-4,5alpha-epoxy-6-methylenemorphinan-3,14diol,hydrochloride salt, also known as nalmefene. STALLING's method, if followed step by step, would have to take much longer than the present invention, and this would result in much greater costs incurred.

FISHMAN, U.S. Pat. No. 3,896,226 claims 6-methylene-6-desoxy dihydro morphine and codeine derivatives and pharmaceutically acceptable salts thereof as a narcotic antagonist composition. However, there are different uses for narcotic antagonists and FISHMAN makes the argument for using his invention as one which "could be administered orally in comparatively small doses." He does state that another object of his invention is to provide a narcotic antagonist which is also capable of being administered parenterally. However, for the purpose of rapid detoxification, it is not enough to simply claim the invention as a narcotic antagonist. FISHMAN states "It thus will be seen that there have been provided compositions and methods for narcotic antagonists which accomplish the various objects of the invention and are well adapted to meet the conditions of practical use." In fact, on Jul. 22, 1975, the date of issue for U.S. Pat. No. 3,896,226, it was not practical to perform rapid narcotic detoxification as claimed in the present invention because the general knowledge necessary for this process was not available then. The references provided herein relating to rapid detoxification from narcotics go back only as far as 1980. More importantly, in order for rapid narcotic detoxification to be performed safely as embodied in the present invention, current standards of anesthesia practice must be adhered to. These standards of practice include the use of pulse oximetry and capnography. The state of technology in 1975 did not make it practical to use pulse oximetry and capnography as is presently used. Pulse oximetry and capnography were not readily available nor where they considered the standard of practice in anesthesia care in 1975. Therefore, it was not practical in 1975 to use nalmefene as embodied in the present invention. FISHMAN's invention as embodied in U.S. Pat. No. 3,896,226 may have been well adapted to meet the conditions of practical use in 1975, but conditions of practical use are different in 1996 than they were in 1975. Therefore, FISHMAN's claims for his said invention do not apply to the present invention which represents a practical and novel use of a previous invention pertaining to current conditions. FISHMAN's claims could only possibly relate to what was practical in 1975, and what is practical in 1996 as relating to the present invention was not practical in 1975.

MELTZER, et al, U.S. Pat. No. 4,535,157 relates to an improved process for the manufacture of the chemical compound embodied in the present invention and does not relate to the new, practical and novel use of said compound as embodied in the present invention.

OBJECTS AND ADVANTAGES

Accordingly, besides the objects and advantages of using nalmefene for rapid narcotic detoxification described in my above patent, some objects and advantages of the present invention are:

(a) to use a narcotic antagonist to detoxify a narcotic addict in a short amount of time;

(b) to medically administer a long acting narcotic antagonist intravenously which increases the practicality and safety of drug administration during rapid narcotic detoxification;

(c) to decrease the likelihood of liver damage by virtue of the fact that nalmefene does not cause hepatocellular damage to the degree that other narcotic antagonists do;

(d) to administer a narcotic antagonist over a short period of time while allowing for its effects to be long-lasting whereby a constant infusion of narcotic antagonist over a long period of time is not needed;

(e) to avoid severe and life threatening complications, such as pulmonary edema, as is seen with other narcotic antagonists;

(f) To allow for the easy continuation of administering narcotic antagonists in oral tablet, capsule or pill form to a human being after he undergoes the detoxification process, which is accomplished by administering a long-acting narcotic antagonist for a short time during the detoxification process, which allows for easy conversion to oral therapy later on;

(g) To improve drug addiction treatment, enhance abstinence from narcotics and to decrease relapse rate to recurrent drug use.

Still further objects and advantages will become apparent from a consideration of the ensuing description.

DESCRIPTION OF THE INVENTION

The present invention is comprised of producing a state of unconsciousness in a human being who is addicted to and currently using exogenous narcotics, monitoring the life functions of said human being in accordance with acceptable standards of anesthesia practice, and administering the narcotic antagonist nalmefene, preferably by intravenous route, such that a withdrawal reaction will be precipitated in said human being that will last a short time, such that said unconscious human being will not consciously be aware of experiencing, or having had experienced, the withdrawal process.

EXAMPLE 1

A narcotic addict will undergo intravenous cannulation by either the peripheral or central venous route, and the appropriate intravenous solution will be infused intravenously at the appropriate rate for the size and conditions of the patient. Usual anesthetic monitoring techniques are employed. A medication to induce unconsciousness will be administered, preferably by the intravenous route, in doses appropriate for said human being's weight and medical condition. This medication should be a nonopioid derivative not related to the narcotic classification of drugs. Such a drug may be midazolam, propofol, sodium pentothal, a combination thereof, or other drugs commonly used to induce unconsciousness. Once unconsciousness is achieved, and after stabilization of life function, nalmefene may be administered via the intravenous route. Administration may be preceded by intravenous naloxone in a fashion commonly referred to as a "naloxone challenge," though this step is not absolutely necessary. A naloxone challenge may be administered prior to administration of nalmefene to ascertain whether or not said human being is addicted to narcotics. Another reason for performing a naloxone challenge is because naloxone is expected to exert similar changes in life function to said human being as is nalmefene, but the effects of naloxone are much shorter acting than nalmefene, so if there is an adverse reaction to a narcotic antagonist, the effects of naloxone administration will dissipate more quickly that the effects after nalmefene administration would. After administration of nalmefene, said human being's life functions are monitored until it becomes apparent to the treating physician that the withdrawal reaction has subsided. Evidence of withdrawal may be expected to subside two to six hours after administration of narcotic antagonist. After evidence of withdrawal has subsided, said human being is allowed to regain consciousness. Upon awakening, the acute phase of withdrawal is over and said human being is detoxified from the previously abused exogenous narcotic.

EXAMPLE 2

A narcotic addict will undergo intravenous cannulation by either the peripheral or central venous route, and the appropriate intravenous solution will be infused intravenously at the appropriate rate for the size and conditions of the patient. Monitors of life function shall be attached to the patient which may include a pulse oximeter, electrocardiogram patches, a blood pressure cuff attached to a sphygmomanometer and a means to measure the carbon dioxide of said addict's exhaled breath by way of capnography. A medication to induce unconsciousness will be administered, preferably by the intravenous route, in doses appropriate for said human being's weight and medical condition. This medication should be a nonopioid derivative not related to the narcotic classification of drugs. Such a drug may be midazolam, propofol, sodium pentothal, a combination thereof, or other drugs commonly used to induce unconsciousness. A dose of 0.3 milligrams of midazolam per kilogram of said addict's weight administered intravenously may be sufficient to produce unconsciousness. This may be followed by intravenous administration of a medication such as a depolarizing or non-depolarizing neuromuscular blocking agent to facilitate intubation of said addict's trachea. The endotracheal tube is then secured in the correct anatomic position using usual anesthetic care measures. After stabilization of said addict's life functions as usually done in routine anesthetic management, the patient may be administered nalmefene, by continuous intravenous infusion. For a 70 kilogram adult male, the typical initial rate of said nalmefene infusion would consist of infusing 1.5 milligrams of nalmefene over two hours. Said infusion rate of nalmefene may be titrated upward or downward depending on the response of said addict's sympathetic nervous system as evidence by monitoring of life functions and other clinical criteria. After two hours, the nalmefene infusion would typically be discontinued. Some time thereafter, usually no more than four hours after said infusion of nalmefene is complete, the patient can be expected to be detoxified and can be safely rendered back to a state of consciousness. Upon awakening the acute phase of withdrawal will have been completed.

EXAMPLE 3

A narcotic addict will undergo intravenous cannulation by either the peripheral or central venous route, and the appropriate intravenous solution will be infused intravenously at the appropriate rate for the size and conditions of the patient. Monitors of life function shall be attached to the patient which may include a pulse oximeter, electrocardiogram patches, a blood pressure cuff attached to a sphygmomanometer and a means to measure the carbon dioxide of said addict's exhaled breath by way of capnography. A medication to induce unconsciousness will be administered, preferably by the intravenous route, in doses appropriate for said human being's weight and medical condition. This medication should be a nonopioid derivative not related to the narcotic classification of drugs. Such a drug may be midazolam, propofol, sodium pentothal, a combination thereof, or other drugs commonly used to induce unconsciousness. Typically, 3–5 milligrams of sodium pentothal per kilogram of said addict's weight could be administered for this purpose of producing unconsciousness. This may be followed by administration of a neuromuscular junction blocking agent to facilitate intubating said addict's trachea, though said neuromuscular junction blocking agent may not be necessary. If a neuromuscular junction blocking agent is used, it is preferable to use a short-acting agent such that signs of motor agitation and piloerection are not masked during the detoxification procedure. The endotracheal tube is then secured in the correct anatomic position using usual anesthetic care measures. After stabilization of said addict's life functions as usually done in routine anesthetic management, the patient may be administered nalmefene in small incremental intravenous bolus doses as determined by the physician's interpretation of the response of said addict's monitored life functions and other clinical parameters, up to a maximum dose of 1.5–2.0 milligrams for a 70 kilogram adult male. The end point of nalmefene-induced narcotic detoxification can be considered when said addict appears to have no further evidence of acute withdrawal after at least 0.5 to 1.5 milligrams of nalmefene have been given over a short period of time. Said other clinical parameters may include looking for the following clinical signs: mydriasis, vomiting, motor agitation, lacrimation, rhinorrhea, diaphoresis and piloerection. Life functions include but are not limited to blood pressure and heart rate.

Having thus described the present invention there is claimed as new and desired to be secured by Letters Patent:

1. A method for detoxifying a patient who is addicted to and who is currently using exogenous narcotics, said method comprising the steps of:

(a) anesthetizing the patient to produce a state of unconsciousness;

(b) inducing acute withdrawal by administering nalmefene; and (c) allowing the patient to regain consciousness after acute withdrawal is complete.

2. The method of claim 1, wherein the nalmefene is administered intravenously.

3. The method of claim 2, Wherein the nalmefene is administered by intravenous infusion.

4. The method of claim 2, wherein the nalmefene is administered by incremental intravenous bolus doses.

5. The method of claim 2, wherein the nalmefene is administered intravenously over of period of about two hours.

6. The method of claim 1, wherein step (b) is further characterized in that the nalmefene is administered in an amount ranging from about 0.5–1.5 mg to no more than about 1.5–2.0 mg based on the weight of a 70 kg adult male.

* * * * *